(12) United States Patent
Yehualaeshet et al.

(10) Patent No.: US 9,434,976 B2
(45) Date of Patent: Sep. 6, 2016

(54) MODIFICATION OF SAMPLE PREPARATION TO DIFFERENTIATE LIVE AND DEAD BACTERIA BY POLYMERASE CHAIN REACTION ASSAY

(71) Applicant: Tuskegee University, Tuskegee, AL (US)

(72) Inventors: Teshome Yehualaeshet, Tuskegee, AL (US); Temesgen Samuel, Tuskegee, AL (US); Woubit Abdela, Tuskegee, AL (US); Tsegaye Habtemariam, Tuskegee, AL (US)

(73) Assignees: TUSKEGEE UNIVERSITY, Tuskegee, AL (US); Tsegaye Habtermariam, Tuskegee, AL (US)

( * ) Notice: Subject to any disclaimer, the term of this patent is extended or adjusted under 35 U.S.C. 154(b) by 0 days.

(21) Appl. No.: 14/278,902

(22) Filed: May 15, 2014

(65) Prior Publication Data
US 2014/0342366 A1 Nov. 20, 2014

Related U.S. Application Data

(60) Provisional application No. 61/823,535, filed on May 15, 2013.

(51) Int. Cl.
  *C12Q 1/68* (2006.01)
  *C12Q 1/04* (2006.01)
  *C07H 21/02* (2006.01)

(52) U.S. Cl.
  CPC ..................................... *C12Q 1/04* (2013.01)

(58) Field of Classification Search
  CPC ....................................................... C12Q 1/00
  See application file for complete search history.

(56) References Cited

PUBLICATIONS

Soejima, T. et al., J. Clin. Microbiol., vol. 46, pp. 2305-2313 (2008).*

* cited by examiner

*Primary Examiner* — Teresa E Strzelecka
(74) *Attorney, Agent, or Firm* — Hogan Lovells US LLP

(57) ABSTRACT

The invention relates to a method of determining whether a live microbe, such as bacteria, is present in a test sample.

9 Claims, 4 Drawing Sheets

Figure 1

Principle of DNA intercalating chemicals modification to detect
only viable bacteria by qPCR Live Bacteria + GelRed™      DNA Extraction/PCR      PCR Product Live Bacteria + NO GelRed™   DNA Extraction/PCR      PCR Product Dead Bacteria + GelRed™      DNA Extraction/PCR      NO PCR Product Dead Bacteria + NO GelRed™   DNA Extraction/PCR      PCR Product Real time PCR results of live, heat- or isopropyl alcohol-killed E. Coli at different concentrations of compound CE (Gel Red™).

Real time PCR result of live, heat- or isopropyl alcohol-killed L. monocytogens at different concentrations of compound CE (Gel Red™).

Real time PCR results of live, heat- or isopropyl alcohol Salmonella typhimurium at different concentrations of compound CE (Gel Red™).

SEQUENCE LISTING

<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
aagattgcgc tgaagccttt g                                      21

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
cattggcatc gtgtggacag                                        20

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
tgcgcaacaa actgaagcaa a                                      21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
catccgcgtg tttcttttcg a                                      21

<210> SEQ ID NO 5

```
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcccatttct ccgcaccatt tgat                                           24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctgaacgctt tcgaccgttt ggtt                                           24
```

MODIFICATION OF SAMPLE PREPARATION TO DIFFERENTIATE LIVE AND DEAD BACTERIA BY POLYMERASE CHAIN REACTION ASSAY

The instant application contains a Sequence Listing which has been submitted electronically in ASCII format and is hereby incorporated by reference in its entirety. Said ASCII copy, created on Jul. 22, 2014, is named 57193-0022_SL.txt and is 1,769 bytes in size.

BACKGROUND OF THE INVENTION

Differentiation of live and dead cells is an important challenge in microbial diagnostics. In the case of pathogenic microorganisms, the potential health risks are limited to the live portion of a mixed microbial population. Four physiological states of microbes can be distinguished in flow cytometry using fluorescent stains: 1) reproductively viable; 2) metabolically active; 3) intact; and 4) permeabilized cells. Depending on the conditions, all stages except the permeabilized cells can have the potential of recovery upon resuscitation and thus have to be considered potentially live. DNA-based diagnostics tend to overestimate the number of live cells because they will also measure the DNA from dead cells, due in part to the relatively long persistence of DNA after cell death (e.g. up to 3 weeks). DNA extracted from a sample can originate from cells in any of the four above mentioned physiological states including the dead permeabilized cells. Thus most DNA-based diagnostics can not distinguish between live and dead bacteria.

The ability to quickly and accurately distinguish between live and dead bacteria is needed by today's challenges of "super-bug" antibiotic-resistance bacteria and terrorist threats of bio-weapons. The standard method in the past has been to take a swab sample of the potentially contaminated area and grow the collected bacteria on a media plate. The resulting colonies were then identified and counted to determine the level of contamination. Growing bacteria on media plates is slow and assumes that the media furnishes the entire necessary nutrient for growth. It was possible for live bacteria not to be detected if the media was not correct for the bacteria or the bacteria were difficult to grow on artificial media.

Traditionally, viability in bacteria is synonymous with the ability to form colonies on solid growth medium and to proliferate in liquid nutrient broths. These traditional, culture-based tests are time-consuming and can work poorly with slow-growing or viable, but non-cultivable organisms. They do not provide real-time results or timely information that is needed in applications such as industrial manufacturing.

Polymerase chain reaction ("PCR") has also been used as tool for the quick detection of bio-threat and foodborne pathogens. However, PCR itself does not discriminate from DNA coming from live pathogens (harmful) or dead pathogens (harmless). Accurate determination of live, damaged or injured, and dead bacteria is important in microbiology detection to avoid false alarm. Dead bacteria present after processes such as pasteurization or disinfections might present no hazard but still can be detected by PCR. Injured cells are virulent and may or may not be detected by standard procedures. PCR offers a more rapid and sensitive method than culture-based techniques, but the major limitation is the lack of differentiating the DNA from live or dead bacteria. In food matrices and the environment, DNA can be very stable and persist for extended periods of time, and therefore, it is desirable to have DNA-based assays that can identify only viable organisms.

In the past, PMA (propidium monoazide) or other DNA intercalating chemicals (such as EMA (ethidium monoazide bromide) or Phenanthridium derivatives have been used to detect only viable bacteria by qPCR. These compounds, though, are expensive, toxic and demand care in handling disposal.

SUMMARY OF THE INVENTION

One embodiment of the invention is a method of determining whether a live microbe, such as a bacteria or fungus is present in a test sample. The method involves isolating microbes from the test sample and exposing them to GelRed™. Then DNA is isolated form the treated microbes and subjected to PCR amplification. If the microbes in the test sample were all dead, then there would be no PCR products after the reaction because the GelRed™ would have intercalated into the DNA, which inhibits a PCR amplification reaction. However, if the test sample contained live microbes, the GelRed™ does not penetrate the cell membrane of the live microbes and thus when the DNA is extracted and subjected to PCR amplification, it is able to be amplified and a PCR reaction product is produced. The presence of a PCR amplification product indicates that the test sample contained live microbes.

Methods of the invention can also be used in many applications, for example, to test the efficacy of treatment with a disinfectant and/or antibiotic on environmental samples and to confirm the safety in food industry. A cell culture is exposed to a candidate disinfectant and/or antibiotic; and then exposed to GelRed™. DNA is isolated from the sample and PCR is performed on the isolated DNA. PCR results are compared between the disinfectant/antibiotic treated cultures with untreated cultures. If the disinfectant/antibiotic worked to kill the microbes, there would not be a PCR product as the GelRed™ would have been able to intercalate into the DNA and stop PCR amplification. If on the other hand, the disinfectant/antibiotic did not work to kill all of the microbes, then there would be a PCR product. Microbes surviving the disinfectant/antibiotic would have had non-intercalated DNA, which would have been amplified. Methods of the invention can be applied to a wide range of microbial species and any other cells where the cell membrane inhibits uptake of the GelRed™ and where the cell membrane of a dead bacteria (e.g. because of perforation) allows the uptake of the intercalating dye (GelRed™).

The invention provides a method of detecting the presence of a live microbe in a test sample suspected of containing the live microbe. The method comprises a) isolating the microbe from the known culture; b) adding GelRed™ dye to the isolated microbe from step (a); c) extracting DNA from the microbe after step (b); d) performing PCR on the DNA from step (c); e) analyzing PCR results from step (d) for the presence or absence of amplified DNA using real time PCR and further gel electrophoresis confirmation; and f) correlating the presence of amplified DNA from step (e) with the presence of live bacteria in the test sample. It may be desirable to further confirm that no viable bacteria were present by culturing on an appropriate media after heat and isopropyl alcohol inactivation of the culture.

In certain embodiments, the microbe is bacteria. In some embodiments, the bacteria is *E. coli* and Gel Red™ is used at a dilution ranging from about 1:1 to about 1:10, wherein the stock solution of Gel Red™ before serial dilutions were performed was 3×. In some embodiments the Gel Red™ is used at a dilution at about 1:10 wherein the stock solution of Gel Red™ before serial dilutions were performed was 3×.

In certain embodiments, the bacteria is *Listeria monocytogenes* and Gel Red™ is used at a dilution ranging from about 1:1 to about 1:10, or 1:10 to about 1:100, wherein the stock solution of Gel Red™ before serial dilutions were performed was 3×.

In certain embodiments, the bacteria is *Salmonella typhimurium* and Gel Red™ is used at a dilution ranging from about 1:1 to about 1:100, wherein the stock solution of Gel Red™ before serial dilutions were performed was 3×. In some embodiments the Gel Red™ is used at a dilution of about 1:100 wherein the stock solution of Gel Red™ before serial dilutions was performed was 3×.

BRIEF DESCRIPTION OF THE FIGURES

FIG. 1 provides a summary of the use of GelRed™ to detect only viable bacteria by qPCR.

DETAILED DESCRIPTION OF THE INVENTION

Figure 2:
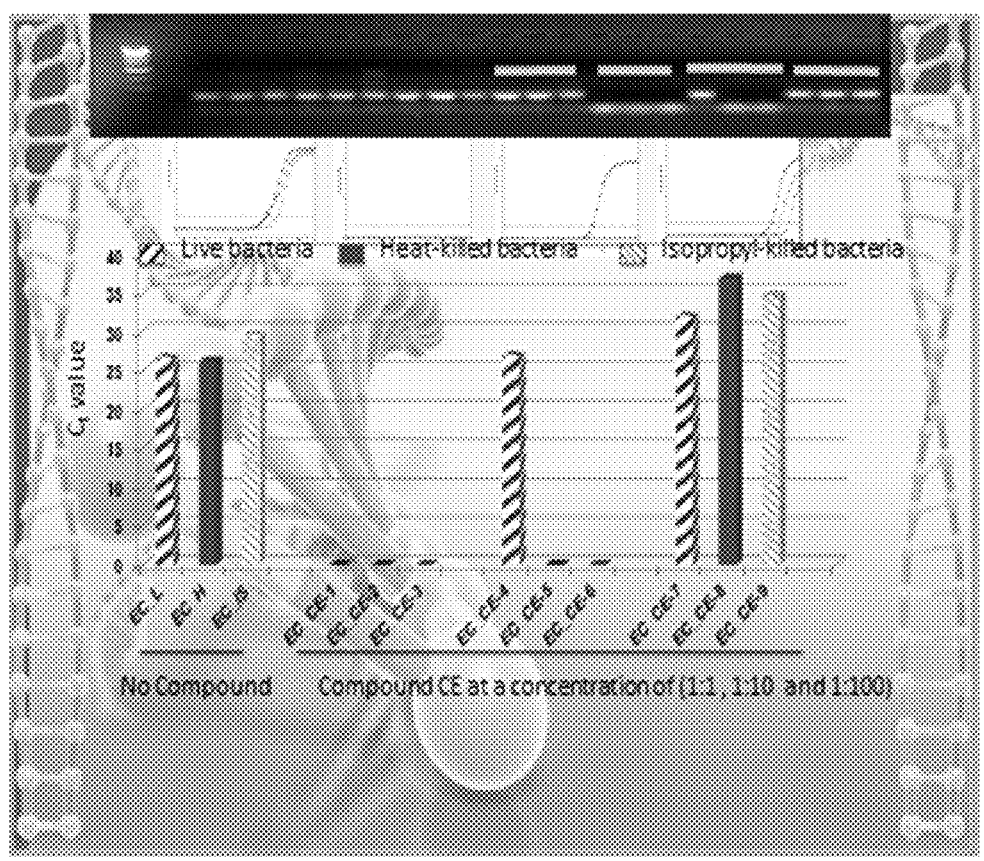
FIG. 2 provides real time PCR results of live, heat- or isopropyl alcohol-killed *E. coli* at different concentrations of compound CE (Gel Red™).

One embodiment of the invention provides a method of detecting the presence of a live microbe in a test sample suspected of containing a dangerous live microbe. The test sample may be generated from any substance such as a liquid, solid, slurry, etc. The test sample could be generated by swabbing an area or product suspected of containing dangerous microbes. Any area of concern could be used to generate a test sample. For example, the test sample could be generated from food products themselves or machinery used in the preparation of food products. The test sample could be generated from a hospital, clinic or doctor's office, as well as from a patient. The test sample could be generated from a swab of any solid surface suspected of harboring a dangerous pathogen such as a counter, table, desk, package, suitcase, computer, telephone, mail, etc.

The test sample is then treated to isolate any microbes that may be contained therein. Methods of isolating microbes from various sample types are known in the art. Gel Red™ is then added to the isolated microbes.

Gel Red™ is a DNA-intercalating chemical that is highly selective in penetrating only into dead bacteria (not live). The penetrating chemical binds with the DNA and blocks amplification of the targeted gene.

Gel Red™ is an ultra sensitive, extremely stable and environmentally safe fluorescent nucleic acid dye designed to replace the highly toxic ethidium bromide (EB) for staining dsDNA, ssDNA or RNA in agarose gels or polyacrylamide gels. A series of safety tests have confirmed that Gel Red™ is noncytotoxic, nonmutagenic and nonhazardous at concentrations well above the working concentrations used in gel staining. As a result, Gel Red™ can be safely disposed of down the drain or in regular trash, providing convenience and reducing cost in waste disposal. Gel Red™ has the IUPAC name of 5, 5'-(6, 22-dioxo-11, 14, 17-trioxa-7, 21-diazaheptacosane-1, 27-diyl)bis(3, 8-diamino-6-phenylphenanthridin-5-ium) iodide and its structure is provided below.

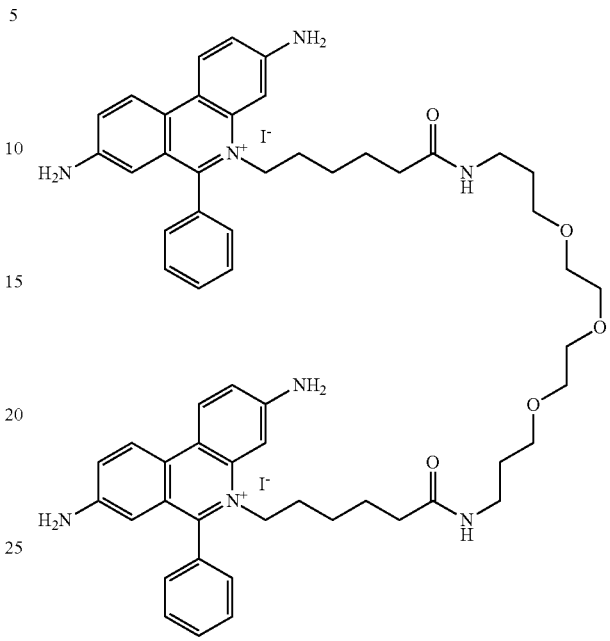

In embodiments of the invention, the Gel Red™ is used at a concentration that penetrates membranes of dead microbes but not the membranes of live microbes. The Gel Red™ dye intercalates into the microbe's DNA and renders the DNA unable to be amplified in a PCR amplification reaction. DNA is then extracted from the microbes in the sample and PCR is performed. In certain embodiments a universal primer is used that is capable of amplifying a wide array of the dangerous microbes in the corresponding test samples. In certain embodiments, more specific primers are chosen which can only amplify a certain microbe. In certain embodiments, specific primes are chosen that have the ability to amplify DNA from a certain class of microbes (e.g. bacteria as opposed to fungi).

The amplification reaction is allowed to proceed for sufficient cycles to allow for sufficient amplification of DNA to allow detection of the amplified DNA. It may be useful to run a standard in the test to determine that sufficient cycles have been run to detect any present DNA. If the sample contained only dead microbes, there would be no amplification product present, as the Gel Red™ would have intercalated into the DNA and rendered the DNA unable to be amplified. If the sample contained a live microbe, there would be an amplification product present as the Gel Red™ would not have entered the live cell membrane and thus would not have any ability to inhibit a PCR amplification reaction. Thus by running the reaction and analyzing the results for the presence of a PCR amplification product, one can quickly determine whether the test sample contained any live microbe.

The test sample could be then further analyzed to identify the type of microbe or if a specific primer had been designed to only amplify a specific type of microbe, then the presence of the amplified product would inform the tester that this particular microbe was present in the test sample and it was present as a live microbe.

FIG. 1 shows that if the test sample contains only live microbes, and Gel Red™ is added, there will be a PCR product. If the test sample contains only dead microbes, and Gel Red™ is added, there will be no PCR product. If the sample contains both live and dead microbes and Gel Red™ is added, then there will be a PCR product (coming from the live microbe DNA only).

Methods of the invention can be used to test a sample for the presences of any microbes containing DNA and a cell membrane, such as, but not limited to, bacteria and fungi.

Figure 3:
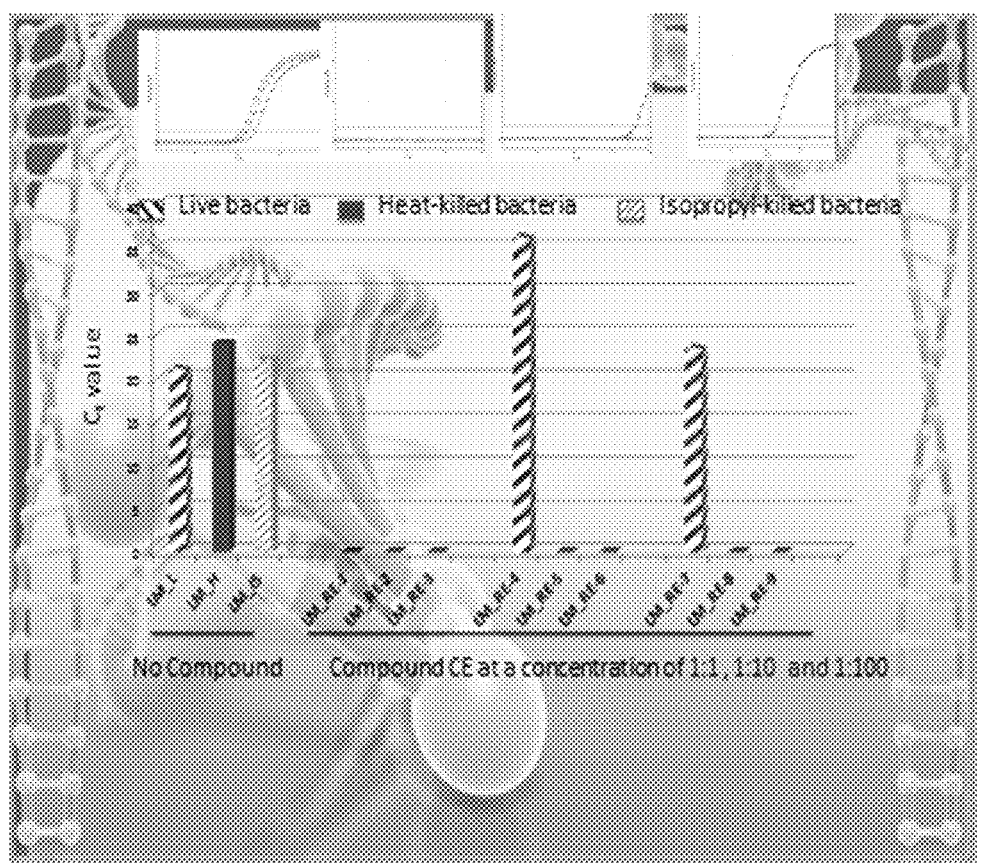
FIG. 3 provides real time PCR result of live, heat- or isopropyl alcohol-killed *L. monocytogens* at different concentrations of compound CE (Gel Red™).
Figure 4:
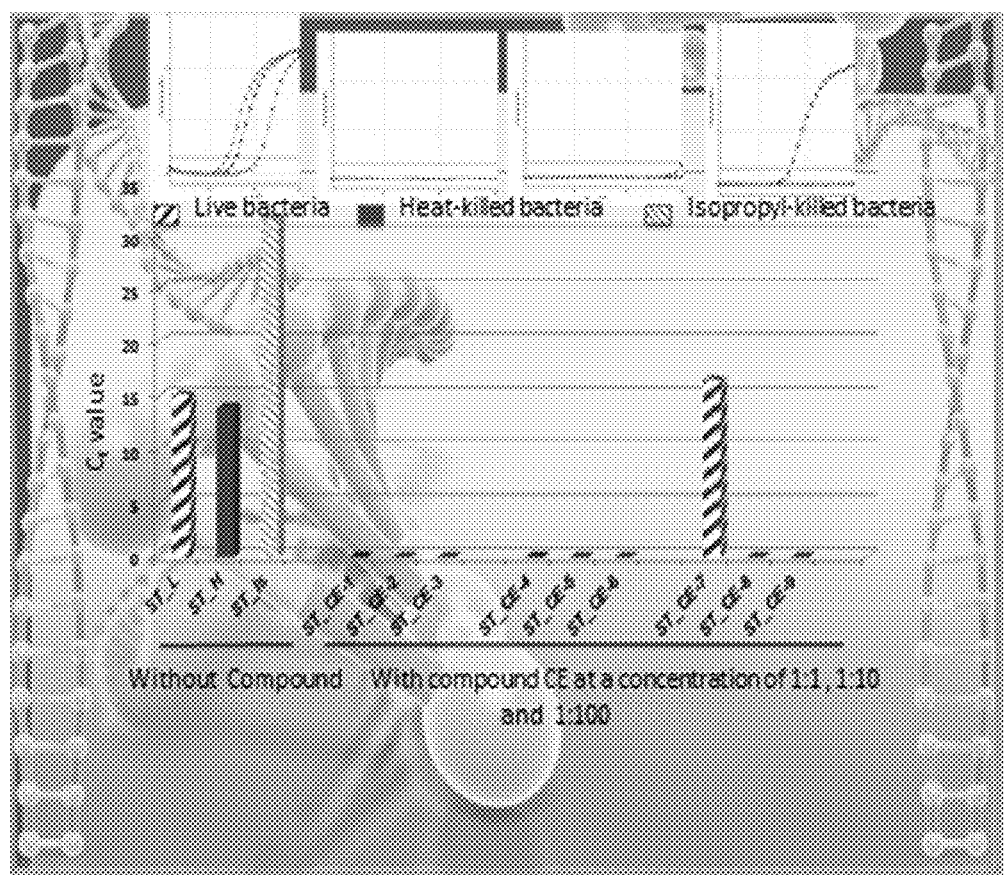
FIG. 4 provides real time PCR results of live, heat- or isopropyl alcohol *Salmonella Typhimurium* at different concentrations of compound CE (Gel Red™).

Various amounts of Gel Red™ can be added to the isolated microbe. Originally the GelRed™ is available at 10,000× solution in water or 3× staining solution in $H_2O$ (working solution). The base for the concentration calculation refers to working solution or 3×. In FIGS. 2-4 various dilutions were reported (1:1, 1:10 and 1:100). "1:1" means where 1.0 µl of commercially available Gel Red™ at 3× is diluted in 1.0 µl diluent (such as water). "1:10" means where 1.0 µl of commercially available Gel Red™ at 3× is diluted in 10.0 µl diluent (such as water). "1:100" means where 1.0 µl of commercially available Gel Red™ at 3× is diluted in 100.0 µl diluent (such as water).

If an excess amount of Gel Red™ is used, it can penetrate live cells and render the tests inaccurate. Often the type of microbe present may dictate the amount of Gel Red™ to use. For example, when testing for the presence of *E. coli*, Gel Red™ at a dilution of 1:1 was too concentrated and there were no PCR products even in the sample containing the live bacteria. The Gel Red™ was too highly concentrated so it killed all of *E. coli* even in the "live sample. FIG. 2 also shows that the 1:100 dilution was too weak as there were amplification products in all samples, including the killed bacteria samples. The Gel Red™ was too weak to get into the intact cell membrane of the live *E. coli*. The dilution of 1:10 worked as it generated a signal from live but not from killed samples. See example 1 and FIG. 2.

*E. coli* is a Gram-negative, rod-shaped bacterium that is commonly found in the lower intestine of warm-blooded organisms. Most *E. coli* strains are harmless, but some serotypes can cause serious food poisoning in humans, and are occasionally responsible for product recalls due to food contamination.

When testing for the presence of *L. monocytogens*, Gel Red™ at a dilution of 1:1 did not work as it was too strong and penetrated into the pathogen so there were no PCR products. At a dilution of 1:10 and 1:100 there was a signal from live but not from killed samples. See example 2 and FIG. 3. *Listeria monocytogenes* is a gram-positive bacteria and it causes the infection listeriosis. It is a facultative anaerobic bacterium, capable of surviving in the presence of oxygen. It can grow and reproduce inside the host's cells and is one of the most virulent food-borne pathogens, with 20 to 30 percent of clinical infections resulting in death. Responsible for approximately 2,500 illnesses and 500 deaths in the United States (U.S.) annually, listeriosis is the leading cause of death among foodborne bacterial pathogens, with fatality rates exceeding even *Salmonella* and *Clostridium botulinum*.

When testing for the presence of *Salmonella Typhimurium*, Gel Red™ at a dilution of 1:1 and 1:10 did not work as it was too strong and penetrates the pathogen so there were no PCR products (and thus could not differentiate between live and dead *Salmonella Typhimurium*). At a dilution of 1 1:100 there was a signal from live but not from killed samples. See example 3 and FIG. 4.

*Salmonella Typhimurium* is a pathogenic Gram-negative bacteria predominately found in the intestinal lumen. Its toxicity is due to an outer membrane consisting largely of lipopolysaccharides (LPS), which protect the bacteria from the environment. *Salmonella Typhimurium* causes gastroenteritis in humans and other mammals. When the bacterial cells enter epithelial cells lining the intestine they cause host cell ruffling which temporarily damages the microvilli on the surface of the cell. This causes a rush of white blood cells into the mucosa, which throws off the ratios between absorption and secretion, and leads to diarrhea.

An advantage of the present invention is that Gel Red™ is cheap, safer and less toxic than PMA and EMA. In addition to the tests run for Gel Red™, the inventors also ran tests using PMA and EMA. It was discovered that PMA/EMA penetrates only live *E. coli* at its recommended concentration and it blocks PCR amplification. PMA completely blocks the amplification of DNA from dead *E. coli*, *L. monocytogens* and *S. typhimurium* and it has been reported that further modification may be needed to make the output consistent (Sungwoo Bae and Stefan Wuertz. Discrimination of Viable and Dead Fecal Bacteroidales Bacteria by Quantitative PCR with Propidium Monoazide. Appl Environ Microbiol. 2009 May; 75(9): 2940-2944.PMCID: PMC2681701). The inventors also discovered that the DNA amount difference and the inactivation/killing method of the bacteria did not have any substantial influence to the Gel-Red-qPCR outcome pattern, whereas the concentration of the DNA binding chemicals (GelRed™) did influence the qPCR outcome. A comparison of Gel Red™, PMA and EMA is provided below.

TABLE 1

| Chemical | Description | Solubility/Stability | Cost/application |
|---|---|---|---|
| Propidium monoazide (PMA) | PMA is EMA derivative - high affinity photoreactive DNA binding dye. Becomes highly fluorescent upon binding to nucleic acids resulting in permanent DNA modification Displayed substantially lower cytotoxicity Impermeant to live cells. | Soluble in water Should be stored at −20° C. protected from light. Stable at the recommended | Expensive compared to CE |
| Ethidium monoazide bromide (EMA) | Cell membrane-impermeable | Soluble in DMF or EtOH. Store at 4° C. and protect from light at all times. Potentially harmful | Same as PMA |

TABLE 1-continued

| Chemical | Description | Solubility/Stability | Cost/application |
|---|---|---|---|
| Chemical E (C-E) | DNA-binding chemical. Nonmutagenic and noncytotoxic. No need of exercising special precaution. | Soluble and stable in water, and under normal light (photostable). Disposal as regular trash | Much cheaper and affordable for routine application than PMA and EMA |

EXAMPLES

Bacterial species included in these experiments were *E. coli*, *L. monocytogens*, and *S. Typhimurium*. Fresh culture was suspended in a buffer and placed in three tubes (live bacteria, heat-killed and isopropanol-killed bacteria). The first tube contained live bacteria without treatment, and the second and the third tube were inactivated by heat and isopropanol, respectively. The DNA-intercalating chemicals used in this experiment were PMA, EMA and other DNA-binding chemicals, which were not previously reported. The experiments were performed to study the application of sample modification with DNA-binding chemicals to enable PCR to amplify samples only from viable bacteria. The initial result showed that sample modified with PMA and EMA can block the amplification of DNA from dead bacteria (*E. coli, L. monocytogens* and *S. typhimurium*). The bacterial sample was modified with PMA or combined with high voltage light exposure to assess the combined treatment effect. The results showed that the use of PMA combined with light exposure was not much different from using only PMA.

Additional to PMA and EMA, twenty-one other DNA-binding chemicals were tested to assess their use as alternate in PCR sample modification. The concentration of the chemicals, which can only amplify DNA from viable cells, was determined for different bacterial spp. Compound CE (which is GelRed™) was found to have similar advantages like PMA and it is not previously documented for PCR application. Compared to PMA, compound CE (GelRed™) is safe and easy for translational application as a routine protocol. See Table 1.

The methods presented here overcome the currently missing knowledge gap to detect only viable cells by PCR. The output of this novel approach will be extremely useful for the detection of only viable pathogens by PCR assay, which is demanding in food safety and other disciplines. No end product of PCR from dead cells is necessary in the food industry or bedside, and the FDA requests the complete inhibition of PCR product from dead bacteria.

Example 1

*Escherichia coli* O157:H7

A sample containing *E. coli* was tested. One sample included live *E. coli*. Another sample included heat killed *E. coli* and another sample contained isopropyl alcohol killed *E. coli*. See FIG. 2. In FIG. 2, Compound CE stands for Gel Red™. Real time PCR was run on the samples. When Gel Red™ was used at a 1:10 dilution, it shows that the sample containing the live bacterial had a PCR amplification product whereas the samples containing the heat killed bacteria did not. FIG. 2 also shows that a dilution of 1:1 was too concentrated and there were no PCR products even in the sample containing the live bacteria. The Gel Red™ was too highly concentrated that it penetrated all of *E. coli* even in the "live sample. FIG. 2 also shows that the 1:100 dilution was too weak as there were amplification products in all samples, including the killed bacteria samples. The Gel Red™ was too weak to get into the intact cell membrane of the live *E. coli*. The dilution of 1:10 worked as got a signal from live but not from killed samples In this reaction, the amplification was run using primers that targeted the per gene (which encodes perosamine synthetase). See Table 2.

Example 2

*Listeria monocytogenes*

A sample containing *L. monocytogenes* was tested. One sample included live *L. monocytogenes*. Another sample included heat killed *L. monocytogenes* and another sample contained isopropyl alcohol killed *L. monocytogenes*. See FIG. 3. In FIG. 3, Compound CE stands for Gel Red™. Real time PCR was run on the samples. The Gel Red™ at a dilution of 1:1 did not work as it was too strong and killed all of the pathogen so there were no PCR products. At a dilution of 1:10 and 1:100 there was a signal from live but not from killed samples.

In this reaction, the amplification was run using primers that targeted the Hly 9125 gene (which encodes listeriolysin O protein). See Table 2.

Example 3

*Salmonella Typhimurium*

A sample containing *Salmonella Typhimurium* was tested. One sample included live *Salmonella Typhimurium*. Another sample included heat killed *Salmonella Typhimurium* and another sample contained isopropyl alcohol killed *Salmonella Typhimurium*. See FIG. 4. In FIG. 4, Compound CE stands for Gel Red™. Real time PCR was run on the samples. The Gel Red™ at a dilution of 1:1 and 1:10 did not work as it was too strong and penetrated all of the pathogen so there were no PCR products (and thus could not differentiate between live and dead *Salmonella Typhimurium*. At a dilution of 1:100 there was a signal from live but not from killed samples.

In this reaction, the amplification was run using primers that targeted the ycdC gene (which encodes a putative transcriptional repressor protein). See Table 2.

TABLE 2

| Bacterial Species | Target Gene (Amplicon size, bp) | Primer Target Gene (Sequence 5'-3') | Gene Function |
|---|---|---|---|
| *Escherichia coli* O157: H7 | Per (497) | Forward: AAG ATT GCG CTG AAG CCT TTG (SEQ ID NO: 1) Reverse: CAT TGG CAT CGT GTG GAC AG (SEQ ID NO: 2) | Codes for perosamine synthetase protein |

TABLE 2-continued

| Bacterial Species | Target Gene (Amplicon size, bp) | Primer Target Gene (Sequence 5'-3') | Gene Function |
|---|---|---|---|
| *Listeria monocytogenes* | Hly (125) | Forward: TGC GCA ACA AAC TGA AGC AAA (SEQ ID NO: 3) Reverse: CAT CCG CGT GTT TCT TTT CGA (SEQ ID NO: 4) | Codes for listeriolysin O Protein |
| *Salmonella typhimurium* | ycdC (142) | Forward: GCC CAT TTC TCC GCA CCA TTT GAT (SEQ ID NO: 5) Reverse: CTG AAC GCT TTC GAC CGT TTG GTT (SEQ ID NO: 6) | Codes for putative transcriptional repressor protein |

The invention claimed is:

1. A method of detecting the presence of a live microbe in a test sample suspected of containing the live microbe, the method comprising:
   a) isolating the microbe from the known culture;
   b) adding 5, 5'-(6, 22-dioxo-11, 14, 17-trioxa-7, 21-diazaheptacosane-1, 27-diyl) bis (3, 8-diamino-6-phenylphenanthridin-5-ium) iodide dye to the isolated microbe from step (a);
   c) extracting DNA from the microbe after step (b);
   d) performing PCR on the DNA from step (c);
   e) analyzing PCR results from step (d) for the presence or absence of amplified DNA using real time PCR and further gel electrophoresis confirmation;
   f) correlating the presence of amplified DNA from step (e) with the presence of live bacteria in the test sample.

2. The method of claim 1 wherein the microbe is bacteria.

3. The method of claim 2 wherein the bacteria is *E. coli* and wherein 5'-(6, 22-dioxo-11, 14, 17-trioxa-7, 21-diazaheptacosane-1, 27-diyl) bis (3, 8-diamino-6-phenylphenanthridin-5-ium) iodide is used at a dilution ranging from about 1:1 to about 1:10, wherein the stock solution of 5, 5'-(6, 22-dioxo-11, 14, 17-trioxa-7, 21-diazaheptacosane-1, 27-diyl) bis (3, 8-diamino-6-phenylphenanthridin-5-ium) iodide before serial dilutions were performed was 3×.

4. The method of claim 3 wherein 5, 5'-(6, 22-dioxo-11, 14, 17-trioxa-7, 21-diazaheptacosane-1, 27-diyl) bis (3, 8-diamino-6-phenylphenanthridin-5-ium) iodide is used at a dilution at about 1:10.

5. The method of claim 2 wherein the bacteria is *Listeria monocytogenes* and wherein 5, 5'-(6, 22-dioxo-11, 14, 17-trioxa-7, 21-diazaheptacosane-1, 27-diyl) bis (3, 8-diamino-6-phenylphenanthridin-5-ium) iodide is used at a dilution ranging from about 1:1 to about 1:10, wherein the stock solution of 5, 5'-(6, 22-dioxo-11, 14, 17-trioxa-7, 21-diazaheptacosane-1, 27-diyl) bis (3, 8-diamino-6-phenylphenanthridin-5-ium) iodide before serial dilutions were performed was 3×.

6. The method of claim 2 wherein the bacteria is *Listeria monocytogenes* and wherein the 5, 5'-(6, 22-dioxo-11, 14, 17-trioxa-7, 21-diazaheptacosane-1, 27-diyl) bis (3, 8-diamino-6-phenylphenanthridin-5-ium) iodide is used at a dilution range of about 1:10 to about 1:100, wherein the stock solution of 5, 5'-(6, 22-dioxo-11, 14, 17-trioxa-7, 21-diazaheptacosane-1, 27-diyl) bis (3, 8-diamino-6-phenylphenanthridin-5-ium) iodide before serial dilutions were performed was 3×.

7. The method of claim 2 wherein the bacteria is *Salmonella typhimurium* and wherein 5, 5'-(6, 22-dioxo-11, 14, 17-trioxa-7, 21-diazaheptacosane-1, 27-diyl) bis (3, 8-diamino-6-phenylphenanthridin-5-ium) iodide is used at a dilution ranging from about 1:1 to about 1:100, wherein the stock solution of 5, 5'-(6, 22-dioxo-11, 14, 17-trioxa-7, 21-diazaheptacosane-1, 27-diyl) bis (3, 8-diamino-6-phenylphenanthridin-5-ium) iodide before serial dilutions were performed was 3×.

8. The method of claim 7 wherein the 5, 5'-(6, 22-dioxo-11, 14, 17-trioxa-7, 21-diazaheptacosane-1, 27-diyl) bis (3, 8-diamino-6-phenylphenanthridin-5-ium) iodide is used at a dilution of about 1:100.

9. The method of claim 1 further comprising the step of confirming that no viable bacteria were present by culturing on an appropriate media after heat and isopropyl alcohol inactivation of the culture.

\* \* \* \* \*